United States Patent
Mullin et al.

(10) Patent No.: US 9,339,516 B2
(45) Date of Patent: May 17, 2016

(54) COMPOSITIONS AND METHODS FOR THE PREVENTION OF ESOPHAGEAL CANCER

(75) Inventors: James M. Mullin, Havertown, PA (US); Jonathan Raines, Gladwyne, PA (US)

(73) Assignees: Lankenau Institute for Medical Research, Wynnewood, PA (US); Monk Street Partners LLC, Collegeville, PA (US)

( * ) Notice: Subject to any disclaimer, the term of this patent is extended or adjusted under 35 U.S.C. 154(b) by 0 days.

(21) Appl. No.: 14/114,236

(22) PCT Filed: May 7, 2012

(86) PCT No.: PCT/US2012/036735
§ 371 (c)(1),
(2), (4) Date: Dec. 31, 2013

(87) PCT Pub. No.: WO2012/154647
PCT Pub. Date: Nov. 15, 2012

(65) Prior Publication Data
US 2014/0113004 A1    Apr. 24, 2014

Related U.S. Application Data

(60) Provisional application No. 61/483,328, filed on May 6, 2011.

(51) Int. Cl.
*A61K 33/30* (2006.01)
*A61K 31/315* (2006.01)
*A61K 9/20* (2006.01)

(52) U.S. Cl.
CPC .............. *A61K 33/30* (2013.01); *A61K 31/315* (2013.01)

(58) Field of Classification Search
None
See application file for complete search history.

(56) References Cited

U.S. PATENT DOCUMENTS

| | | | |
|---|---|---|---|
| 4,894,455 A * | 1/1990 | Hider et al. | 546/2 |
| 2009/0306049 A1 | 12/2009 | Clevers et al. | |
| 2010/0076556 A1 | 3/2010 | Tomantschger et al. | |
| 2010/0094270 A1 | 4/2010 | Sharma | |
| 2010/0272779 A1 * | 10/2010 | Jackson | 424/423 |
| 2010/0285098 A1 | 11/2010 | Haley | |

OTHER PUBLICATIONS

Guy, N., et al., "A Novel Dietary-Related Model of Esophagitis and Barrett's Esophagus, a Premalignant Lesion," Nutrition and Cancer, 59(2), Copyright © 2007, pp. 217-227.*
Saito, Y., et al. "Usefulness of biodegradable stents constructed of poly-l-lactic acid monofilannents in patients with benign esophageal stenosis." World J Gastroenterol. Aug. 7, 2007;13(29):3977-80.
Fong, L.Y., et al. "Zinc supplementation suppresses 4-nitroquinoline 1-oxide-induced rat oral carcinogenesis." Carcinogenesis. Apr. 2011;32(4):554-60. Epub Jan. 18, 2011.
Barrett's Esophagus. National Digestive Diseases Information Clearinghouse (NDDIC). Feb. 17, 2012. 7 pages. Retrieved from the internet on Jun. 12, 2013. <URL:http://digestive.niddk.nih.gov/ddiseases/pubs/barretts/>.
Sampliner, R.E. "New Treatments for Barrett's esophagus." Seminars in Gastrointestinal Disease (1997) 8(2):68-74.
Valenzano, M.C., et al. "Drug Delivery of Zinc to Barrett's Metaplasia by Oral Administration to Barrett's Esophagus Patients" Therapeutic Delivery (2014) 5(3):257-264.
Fong, L.Y.Y., et al. "Esophageal Cancer Prevention in Zinc-Deficient Rats: Rapid Induction of Apoptosis by Replenishing Zinc" (2001) Journal of the National Cancer Institute 93(20):1525-1533.
Taccioli, C., et al. "Zinc Replenishment Reverses Overexpression of the Proinflammatory Mediator S100A8 and Esophageal Preneoplasia in the Rat", Gastroenterology (2009) 136(3):953-966.
Bansal, A., et al. "Treatment of GERD Complications (Barrett's, peptic stricture) and Extra-oesophageal Syndromes", Best Practice & Research Clinical Gastroenterology (2010) 24(6):961-968.

* cited by examiner

*Primary Examiner* — Tracy Vivlemore
*Assistant Examiner* — Monica Shin
(74) *Attorney, Agent, or Firm* — Robert C. Netter, Jr.; Dann, Dorfman, Herrell & Skillman

(57) ABSTRACT

Methods of inhibiting Barrett's esophagus and/or adenocarcinoma in a subject are provided. In a particular embodiment, the method comprises administering at least one composition comprising at least one zinc compound and at least one pharmaceutically acceptable carrier to the esophagus of the subject. The zinc may be a pharmaceutically acceptable salt of zinc, such as zinc gluconate. The zinc may be administered, for example, orally, topically, or by an implantable medical device. In a particular embodiment, the methods further comprise administering at least one analgesic, anesthetic, or other therapeutic agent or therapy for the treatment of Barrett's esophagus. The method may further comprise monitoring the progression of Barrett's esophagus in the subject.

12 Claims, 5 Drawing Sheets

COMPOSITIONS AND METHODS FOR THE PREVENTION OF ESOPHAGEAL CANCER

Figure 1A:
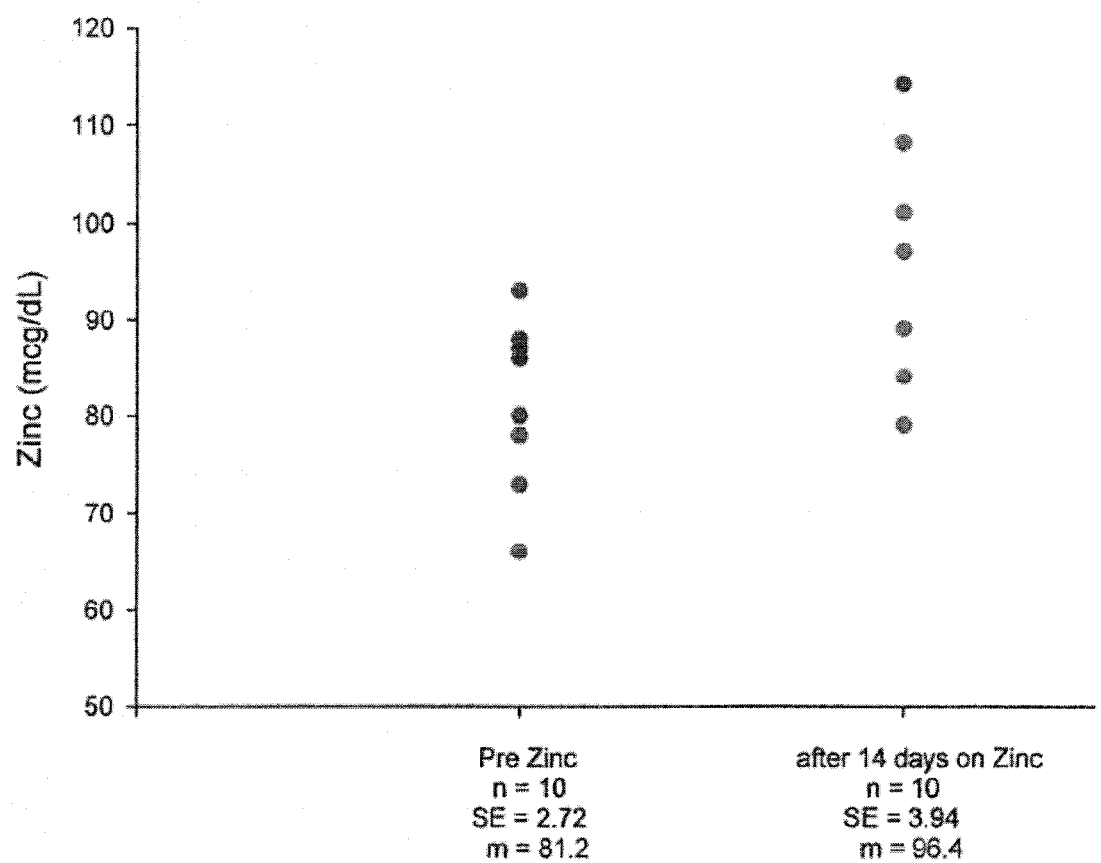

This application is a §371 application of PCT/US2012/036735, filed May 7, 2012, which claims priority under 35 U.S.C. §119(e) to U.S. Provisional Patent Application No. 61/483,328, filed May 6, 2011. The foregoing applications are incorporated by reference herein.

FIELD OF THE INVENTION

The present invention relates to the field of cancer prevention. Specifically, compositions and methods for slowing and/or inhibiting Barrett's esophagus progression to its associated adenocarcinoma are disclosed.

BACKGROUND OF THE INVENTION

Several publications and patent documents are cited throughout the specification in order to describe the state of the art to which this invention pertains. Each of these citations is incorporated herein by reference as though set forth in full.

There is currently no clinically proven therapy to delay or inhibit esophageal cancer progression in the Barrett's esophagus patient. The only approach recommended by the medical community is for the Barrett's patient to undergo endoscopic examination approximately every three years to observe for appearance of carcinoma. This is done grossly and through histology of randomly taken biopsies. Patients with dysplasia typically undergo mucosal resection or laser ablation of the affected tissue, a procedure with a painful recovery. Improvements in the treatment of Barrett's esophagus and the inhibition of Barrett's esophagus related adenocarcinoma are desired.

SUMMARY OF THE INVENTION

In accordance with the present invention, methods of inhibiting Barrett's esophagus and/or adenocarcinoma in a subject are provided. In a particular embodiment, the method comprises administering at least one composition comprising at least one zinc compound and at least pharmaceutically acceptable carrier to the esophagus of the subject. The zinc may be a pharmaceutically acceptable salt of zinc, such as zinc gluconate. The zinc may be administered, for example, orally, topically, or by an implantable medical device. In a particular embodiment, the methods further comprise administering at least one analgesic, anesthetic, or other therapeutic agent or therapy for the treatment of Barrett's esophagus. The method may further comprise monitoring the progression of Barrett's esophagus in the subject.

BRIEF DESCRIPTIONS OF THE DRAWING

Figure 1B:
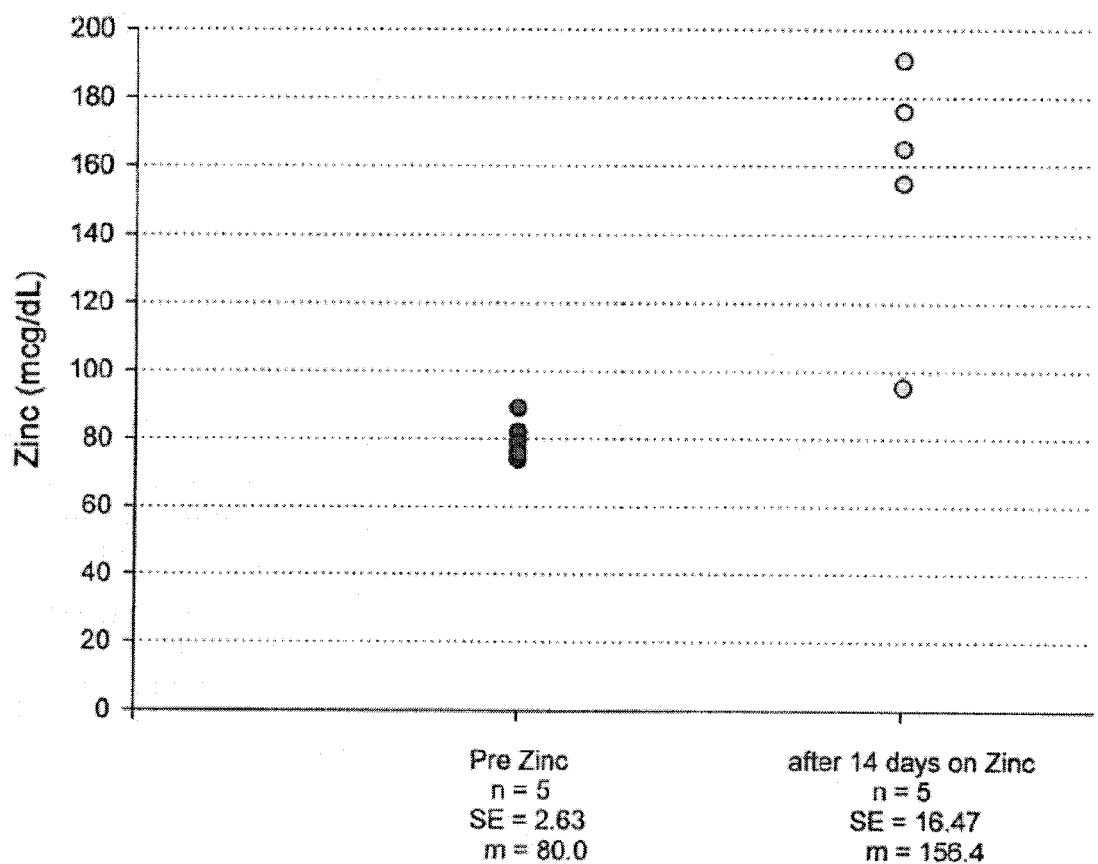

FIGS. 1A and 1B provide graphs of zinc plasma levels in subjects before being administered zinc and after 14 days of zinc administration.

Figure 2:
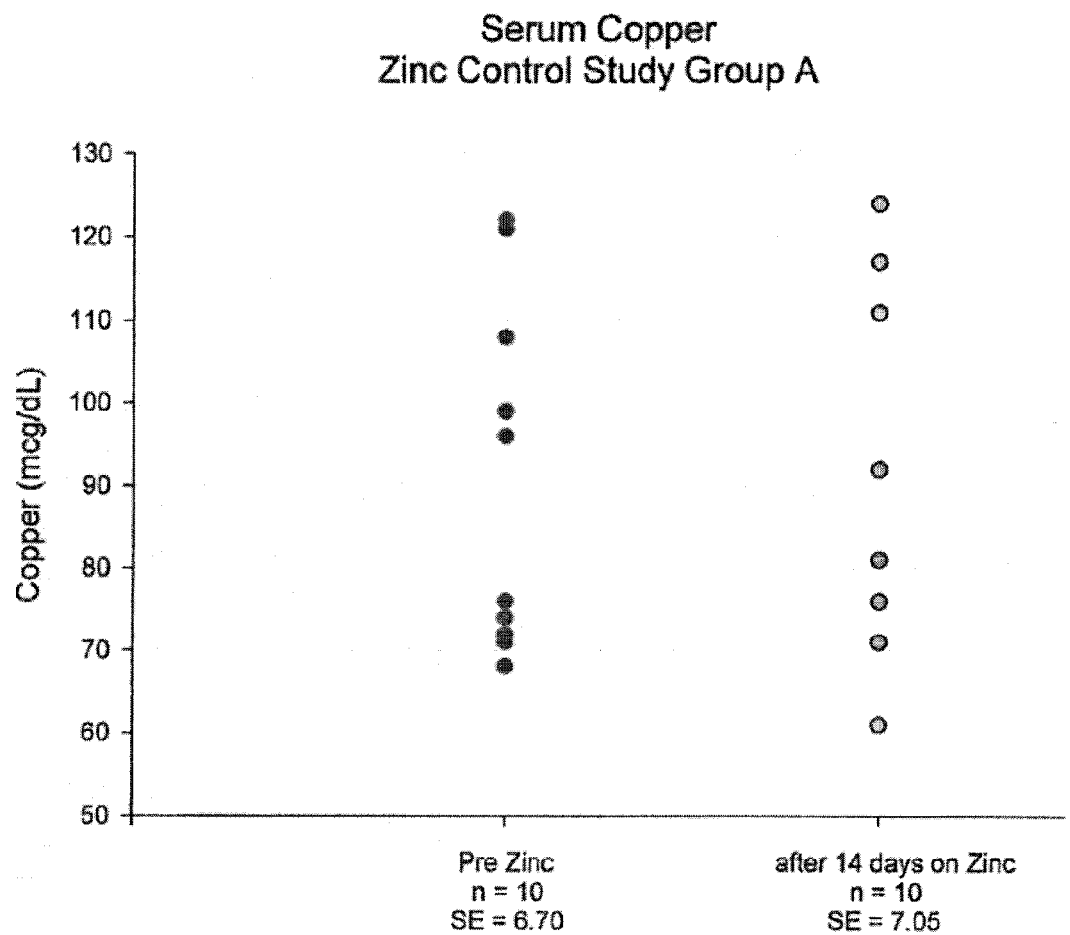

FIG. 2 provides a graph of copper serum levels in subjects before being administered zinc and after 14 days of zinc administration.

Figure 3:
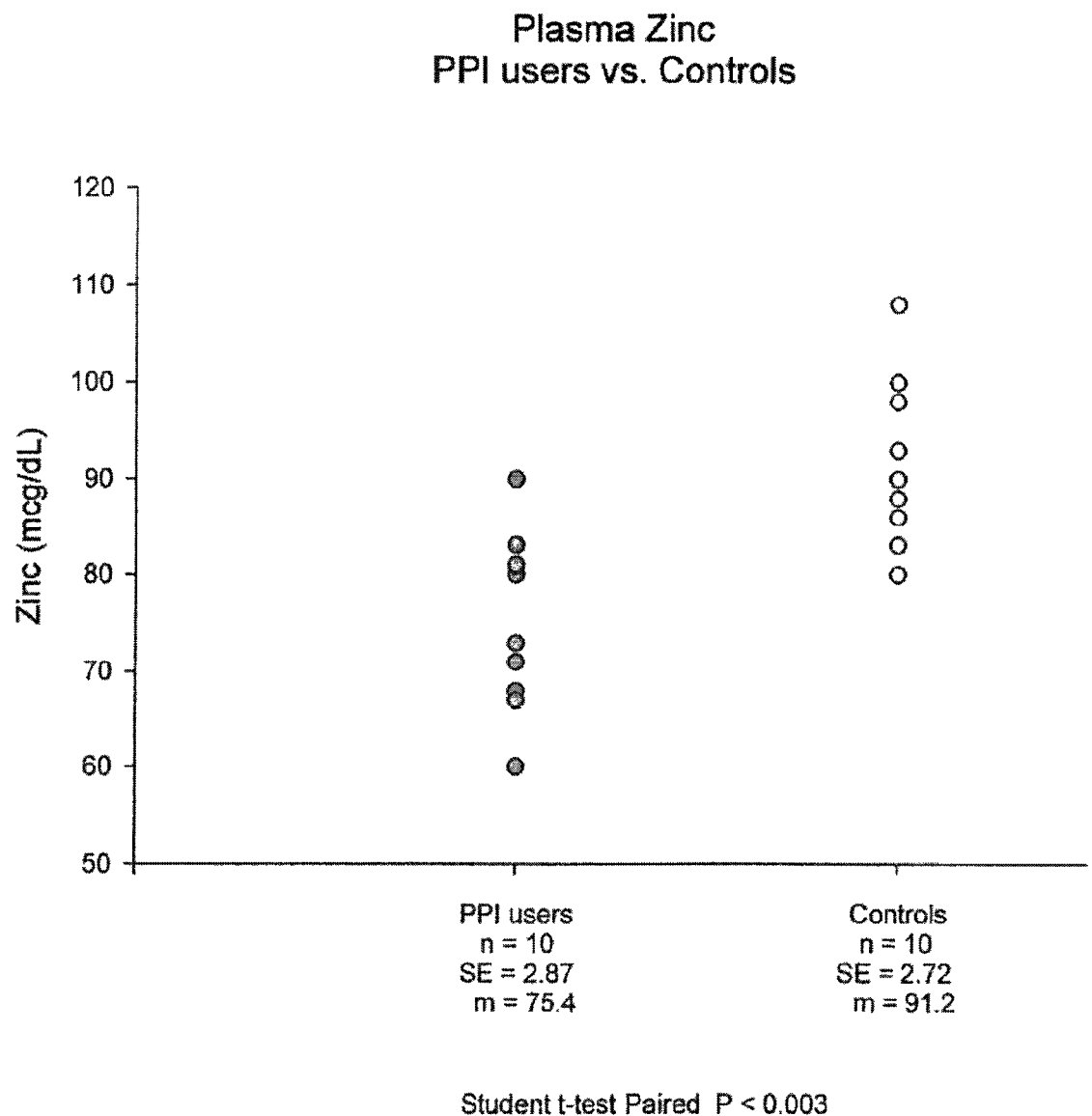

FIG. 3 provides a graph of zinc plasma levels in subjects administered zinc (control) or zinc with a proton pump inhibitor (PPI).

Figure 4:
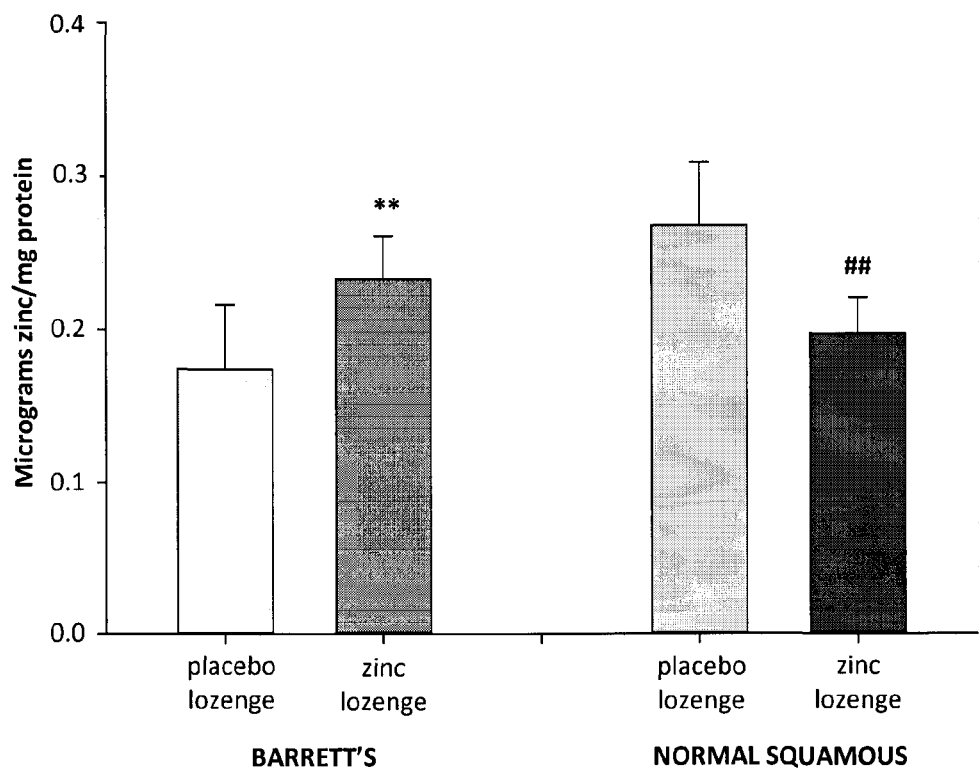

FIG. 4 provides a graph of normalized zinc content of cells from patients given placebo or zinc lozenges. ** P=0.14. ## P=0.08.

DETAILED DESCRIPTION OF THE INVENTION

Barrett's esophagus is a disease in which the lining of the esophagus has been damaged by stomach acid. In Barrett's esophagus, the normal squamous epithelial lining is damaged and abnormal cells grow back within the lesions. The epithelial changes result from chronic regurgitation (reflux) of acidic stomach contents back into the esophagus. As such, subjects who have gastroesophageal reflux disease (GERD) are more likely to have Barrett's esophagus.

Barrett's esophagus is a precancerous condition. Indeed, patients with Barrett's esophagus have a 30-125 fold higher risk of developing cancer of the esophagus than the general population. Typically, cancer in Barrett's esophagus develops in a sequence of changes from nondysplastic epithelium to low-grade (some atypical changes (less than half of cells) but the growth pattern of the glands is still normal) and then high-grade dysplasia (atypical changes in many of the cells and a very abnormal growth pattern of the glands) and then invasive cancer. When dysplasia is present, the risk of developing cancer of the esophagus increases. The type of cancer that occurs with Barrett's esophagus is adenocarcinoma. This is in complete contrast to cancer arising from the squamous lining of the esophagus (squamous cell carcinoma).

Typically, diagnosis and/or monitoring of Barrett's esophagus is performed via endoscopy (upper endoscopy). Barrett's esophagus itself does not cause symptoms. However, since acid reflux causes Barrett's esophagus, those subjects which experience heartburn, particularly over long periods of time (e.g., years), may be screened for Barrett's esophagus. In addition to an endoscopy, Barrett's esophagus may be diagnosed by tissue biopsy and subsequent histological analysis. For example, the presence of goblet cell metaplasia in a biopsy is indicative of Barrett's esophagus.

The instant invention encompasses methods of delaying, inhibiting (reducing, suppressing), treating, and/or preventing adenocarcinoma in a subject, particularly a subject with Barrett's esophagus. The instant invention also encompasses methods of delaying, inhibiting, treating, and/or preventing Barrett's esophagus in a subject. For example, the methods may delay or inhibit the progression of Barrett's metaplasia to dysplasia and adenocarcinoma. The methods of the instant invention comprise administering (directly or indirectly) zinc to the esophagus of the subject. In a particular embodiment, the zinc is delivered orally, topically to the luminal, and/or via an implantable medical device (e.g., a stent). The delivery of zinc has cancer preventative properties and accelerates repair of the Barrett's esophagus.

As stated above, the instant invention encompasses administering zinc to a subject. The zinc may be administered as a complex with another compound. In a particular embodiment, at least one pharmaceutically acceptable salt of zinc is administered to the subject. Zinc salts include, without limitation, a zinc chelate, zinc acetate, zinc butyrate, zinc gluconate, zinc glycerate, zinc glycolate, zinc formate, zinc lactate, zinc picolinate, zinc propionate, zinc salicylate, zinc tartrate, zinc undecylenate, zinc oxide, zinc stearate, zinc citrate, zinc phosphate, zinc carbonate, zinc borate, zinc ascorbate, zinc benzoate, zinc bromide, zinc caprylate, zinc carnosine, zinc chloride, zinc fluoride, zinc fumarate, zinc gallate, zinc glutarate, zinc glycerophosphate, zinc hydroxide, zinc iodide, zinc malate, zinc maleate, zinc myristate, zinc nitrate, zinc phenol sulfonate, zinc picrate, zinc propionate, zinc selenate, zinc succinate, zinc sulfate, zinc titanate, and zinc valerate. In a particular embodiment, the zinc is administered as complexed with gluconate (zinc gluconate).

The zinc of the instant invention may be contained within a composition comprising at least one pharmaceutically acceptable carrier. Common carriers include, without limitation, water, oil, buffered saline, ethanol, polyol (for example, glycerol, propylene glycol, liquid polyethylene glycol and the like), dimethyl sulfoxide (DMSO), detergents, suspending agents, glucose, lactose, gum acacia, gelatin, mannitol, starch paste, magnesium trisilicate, talc, corn starch, keratin, colloidal silica, potato starch, urea, medium chain length triglycerides, dextrans, other carriers suitable for use in manufacturing preparations, in solid, semisolid, or liquid form, and suitable mixtures thereof. In addition excipients and auxiliary, stabilizing, preserving, thickening, flavoring, and coloring agents may be included in the compositions.

As stated above, the zinc of the instant invention may be administered orally. Preferably, the oral administration results in the application (e.g., coating) of the esophagus. Oral compositions of the instant invention may be, for example, a lozenge, troche, a powder/granule, a solution, spray, oral strip (slow or fast release), mouth dissolving tablets (fast melt), a syrup, elixirs, gum, a gel, an emulsion, a dispersion, suspension, a micelle, a liposome, or any other form suitable for oral use. In a particular embodiment, the zinc is administered as a lozenge.

The zinc may also be administered via an implantable device such as a luminal stent, tube, or ring placed within the esophagus (e.g., during an endoscopy). In a particular embodiment, the implantable device is administered to a dyplastic Barrett's esophagus subject. The implantable medical device may be coated with a composition comprising zinc or may elute the composition. In a particular embodiment, the stent is dissolvable or degradable (e.g., a stent that exhibits substantial mass or density reduction or chemical transformation after it is introduced into a subject). In another embodiment, the stent is removable. The stent may be a sustained release device. Examples of esophageal stents include, without limitation, the Boston Scientific Ultraflex™ device, the Medtronic EsophaCoil® device, and the Cook Medical Evolution® device.

The methods may also further comprise the administration of at least one other therapeutic agent or therapy for the treatment of Barrett's esophagus. The other therapeutic agents of therapy may be administered consecutively and/or sequentially with the zinc therapy. Examples of Barrett's esophagus treatment methods include, without limitation, surgical treatment (e.g., of high-grade dysplasia), endoscopic ablation therapy (e.g., for removal of high-grade dysplasia in the esophagus), chemical ablation (e.g., via photodynamic therapy (PDT) for dysplasia (e.g., PDT with porfimer sodium (Photofrin®))), thermal ablation, mechanical ablation, endoscopic mucosal resection, pharmaceutical treatment, or a combination of any of these therapies. Examples of pharmaceutical therapies include the following. WO 2005/012275 describes methods for treating or preventing Barrett's esophagus comprising administering to a mammal in need of such treatment of prevention an effective dose of at least one CCK2 (cholecystokinin) modulator. Further, WO 2005/079778 describes the use of a retinoic acid antagonist in the manufacture of a medicament for the treatment or prevention of Barrett's esophagus. Buttar et al. (Gastroenterology (2002) 122:1101-1112) describe the chemoprevention of esophageal adenocarcinoma by COX-2 inhibitors in an animal model of Barrett's esophagus. U.S. Patent Application Publication No. 2009/0306049 describes methods of treating and inhibiting Barrett's esophagus using Notch pathway inhibitors. In a particular embodiment, the methods further comprise the administration of at least one chemotherapeutic agent.

The methods may also comprise the administration of at least one analgesic and/or anesthetic, particularly when administering the zinc via an implantable medical device such as a stent. In a particular embodiment, the stent further comprises at least one analgesic and/or anesthetic when the zinc containing stent is administered after surgery or treatment to remove the damaged section of the esophagus (e.g., ablation). As stated hereinabove, the ablation procedures to remove Barrett's esophagus tissue are painful. The presence of at least one analgesic and/or anesthetic with the stent reduces the pain experienced by the subject and makes it more likely the subject will consent to undergoing the procedure again, if needed.

The methods of the instant invention may also comprise detecting and monitoring the presence of Barrett's esophagus in the subject. Barrett's esophagus may be detected and monitored by endoscopy and/or biopsy as described hereinabove. Barrett's esophagus may be detected and monitored before, during, and/or after treatment.

The therapeutic agents described herein will generally be administered to a patient as a pharmaceutical preparation. The term "patient" as used herein refers to human or animal subjects. The compositions of the instant invention may be employed therapeutically, under the guidance of a physician.

The compositions comprising the zinc or other therapeutic agent of the instant invention may be conveniently formulated for administration with any pharmaceutically acceptable carrier(s). The concentration of zinc in the chosen medium may be varied and the medium may be chosen based on the desired route of administration of the pharmaceutical preparation. Except insofar as any conventional media or agent is incompatible with the zinc or other therapeutic agent to be administered, its use in the pharmaceutical preparation is contemplated.

The dose and dosage regimen of zinc or other therapeutic agent according to the invention that is suitable for administration to a particular patient may be determined by a physician considering the patient's age, sex, weight, general medical condition, and the specific condition for which the zinc or other therapeutic agent is being administered and the severity thereof. The physician may also take into account the route of administration, the pharmaceutical carrier, and the zinc or other therapeutic agent's biological activity. Selection of a suitable pharmaceutical preparation will also depend upon the mode of administration chosen.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may also be determined by evaluating the toxicity of the molecules in animal models or clinical studies. In a particular embodiment, the amount of zinc administered to the subject (adult) does not exceed 150 mg/day.

The pharmaceutical preparation comprising the zinc or other therapeutic agent may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention:

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y., 1980; and Kibbe, et al., Eds., Handbook of Pharmaceutical Excipients, American Pharmaceutical Association, Washington.

As used herein, the term "subject" refers to an animal, particularly a mammal, particularly a human.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain without a loss of consciousness). Analgesics include opioid analgesics (e.g., codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine) and non-opiate analgesics (e.g., NSAIDs such as salicylates (e.g., aspirin, methyl salicylate, and diflunisal); arylalkanoic acids (e.g., indomethacin, sulindac, diclofenac, and tolmetin); N-arylanthranilic acids (e.g., fenamic acids, mefenamic acid, and mecflofenamate); oxicams (e.g., piroxicam and meloxicam); coxibs (e.g., celecoxib, rofecoxib, valdecoxib, parecoxib, and etoricoxib); sulphonanilides (e.g., nimesulide); naphthylalkanones (e.g., nabumetone); anthranilic acids (e.g., pyrazolidinediones and phenylbutazone); proprionic acids (e.g., fenoprofen, flurbiprofen, ibuprofen, ketoprofen, naproxen, and oxaprozin); pyranocarboxylic acids (e.g., etodolac); pyrrolizine carboxylic acids (e.g., ketorolac); and carboxylic acids.

As used, the term "anesthetic" refers to an agent that produces a reversible loss of sensation in an area of a subject's body. An agent may act as both an analgesic and an anesthetic. Anesthetics include, without limitation, benzocaine, benzyl alcohol, bupivacaine, butamben picrate, chlorprocaine, cocaine, dibucaine, dimethisoquin, dyclonine, etidocaine, hexylcaine, ketamine, lidocaine, mepivacaine, phenol, pramoxine, procaine, tetracaine, salicylates, ropivacaine, prilocaine, and xylocaine.

As used herein, the term "metaplasia" refers to the replacement of one differentiated cell type with another differentiated cell type. Metaplasia is not directly considered carcinogenic.

The term "implantable medical device" refers to any medical device placed inside the human body. The placement of such a device may occur in a body lumen of the patient, such as the esophagus.

The following examples provide illustrative methods of practicing the instant invention, and are not intended to limit the scope of the invention in any way.

EXAMPLE 1

After obtaining Institutional Review Board approval for the study and test subject written informed consent, a short medical and medication history was taken to ascertain that the test subject does or does not meet the study inclusion criteria.

Test subjects contributed a (fasted) venous blood sample (10 cc) prior to supplementation. Test subjects were then placed on supplemental oral zinc (50 mg of zinc/day delivered as 4 zinc gluconate lozenges, 2×/day) for 14 days with instructions not to consume foods that inhibit zinc uptake (e.g., citrus and phytates) when taking supplements. A second, final venous blood sample was taken the morning after (or morning of) the final zinc supplement. Blood samples were collected in EDTA-tubes and were centrifuged to separate out plasma.

Zinc analyses were performed on analytical-grade water dilutions of plasma, using a Perkin Elmer AAnalyst™ Model 800. Atomic absorption measurements were performed using the PerkinElmer AAnalyst™ 800 atomic absorption spectrophotometer equipped with WinLab32™ intuitive software. It utilizes a double beam optical system, solid-sate detector, and deuterium background correction. A single slot air-acetylene 10 cm burner head was used for all measurements. Burner height and fuel gas flow were automatically optimized for each element using the WinLab32™ software. Calibration standards in the range of 0.01 to 0.50 ppm were prepared by dilution of a 1000 ppm Zinc AA standard (Zinc metal in 3% nitric acid) obtained from Ricca Chemical Company. Standards and samples were diluted with Millipore water (>18.2 mega ohms), which also served as the blank. Aspirated standards and samples were measured in triplicate.

The results are provided in FIGS. 1-3. FIGS. 1A and 1B show that zinc plasma levels in subjects orally administered zinc (via lozenges) were significantly higher than in before receiving zinc. These results demonstrate that orally administered zinc is able to enter the blood. FIG. 1A shows zinc plasma levels 12 hours after the last administered zinc dose and FIG. 1B shows zinc plasma levels 2 hours after the last administered zinc dose. As a control, FIG. 2 shows that copper serum levels do not change after a subject has been administered zinc. Lastly, FIG. 3 shows that zinc is blocked from entering the blood after oral administration when administered with an omeprazole family proton pump inhibitor (PPI). This result demonstrates that it is desirable to administer zinc topically to the esophagus when the subject is taking a PPI because the PPI prevents zinc from being effectively and reliably absorbed by the intestine and into the bloodstream.

EXAMPLE 2

10 patients were randomly assigned to placebo lozenge or zinc lozenge classes. After administration of the lozenges (see below), Barrett's tissue biopsies were obtained and flash frozen. The samples were then analyzed by atomic absorption spectroscopy to determine their zinc content. Each sample was also assayed to determine its total protein content. FIG. 4 provides a graph of the amount of zinc in the biopsies, expressed (normalized) on a per protein basis.

FIG. 4 compares the zinc content of Barrett's biopsies for patients administered zinc gluconate lozenges or a placebo. The subjects were administered 4 lozenges per day (for a total zinc content of 53 mg/day) for 14 days prior to an endoscopy and biopsy procurement. Placebo lozenges of sodium gluconate were administered on the same schedule. There is a 30% increase in zinc content in the Barrett's tissue of patients on supplemental zinc for 14 days.

FIG. 4 also shows the zinc content of (adjacent) normal (stratified squamous) esophageal tissue. These normal biopsy samples were procured as well during the endoscopy. Notably, the profile was distinctly different than with the Barrett's biopsies. Normal esophageal tissue actually decreased its zinc content as a result of oral zinc delivery. Without being bound by theory, this likely represents an adaptive response by the normal tissue to lower its intracellular zinc-binding proteins in the presence of increased dietary zinc. The very different response to supplemental zinc by the tissues is indicative of different regulatory responses to the supplemental zinc wherein the precancerous (Barrett's) tissue elevates its zinc content in response to supplemental zinc.

In addition, routine histology (hematoxylin/eosin-stained paraffin sections) was also performed on the Barrett's and normal esophageal tissue biopsies. This was done to confirm that increased zinc delivery is not injurious to either tissue type. Histology shows that neither the Barrett's nor normal tissue is adversely affected by the zinc delivery. The biopsies of tissue from placebo patients and zinc patients appear identical in this regard.

Accordingly, the above demonstrates that zinc delivery is not harmful to the target or neighboring tissue and that oral zinc delivery elevates zinc content of the target tissue.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting the progression of Barrett's esophagus to esophageal adenocarcinoma in a subject, said method consisting of administering zinc to the esophagus of said subject.

2. The method of claim 1, wherein said zinc is a zinc salt.

3. The method of claim 2, wherein said zinc salt is zinc gluoconate.

4. The method of claim 1, wherein said zinc is administered orally.

5. The method of claim 4, wherein said zinc is administered as a lozenge.

6. The method of claim 1, wherein said zinc is administered as a stent implanted in said subject.

7. The method of claim 6, wherein said stent is degradable.

8. A method of inhibiting the progression of Barrett's esophagus to esophageal adenocarcinoma in a subject, said method consisting of the administering zinc and at least one analgesic or anesthetic to the esophagus of said subject.

9. A method of inhibiting the progression of Barrett's esophagus to esophageal adenocarcinoma in a subject, said method consisting of administering zinc to the esophagus of said subject and monitoring the subject for Barrett's esophagus.

10. The method of claim 1, wherein said subject has non-dysplastic Barrett's esophagus.

11. The method of claim 1, wherein said subject has dysplastic Barrett's esophagus.

12. The method of claim 11, wherein said subject has undergone ablation to resect Barrett's esophagus tissue.

* * * * *